United States Patent
Skubsch et al.

(10) Patent No.: US 12,343,422 B2
(45) Date of Patent: Jul. 1, 2025

(54) ACRYLATE AND SILICONE-FREE COSMETIC O/W EMULSION

(71) Applicant: BEIERSDORF AG, Hamburg (DE)

(72) Inventors: Kerstin Skubsch, Prisdorf (DE); Kerstin Franck, Quickborn (DE); Nadine Voigt, Hamburg (DE); Jette Mareike Neben, Hamburg (DE); Svea Wischhoefer, Hamburg (DE); Katharina Herwig, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 796 days.

(21) Appl. No.: 17/753,270

(22) PCT Filed: Jul. 27, 2020

(86) PCT No.: PCT/EP2020/071103
§ 371 (c)(1),
(2) Date: Feb. 25, 2022

(87) PCT Pub. No.: WO2021/037455
PCT Pub. Date: Mar. 4, 2021

(65) Prior Publication Data
US 2022/0323332 A1 Oct. 13, 2022

(30) Foreign Application Priority Data
Aug. 28, 2019 (DE) .................... 10 2019 212 913.7

(51) Int. Cl.
| | | |
|---|---|---|
| *A61Q 19/00* | (2006.01) |
| *A61K 8/06* | (2006.01) |
| *A61K 8/37* | (2006.01) |
| *A61K 8/46* | (2006.01) |
| *A61K 8/73* | (2006.01) |
| *A61K 8/92* | (2006.01) |
| *A61Q 19/10* | (2006.01) |

(52) U.S. Cl.
CPC .............. *A61K 8/732* (2013.01); *A61K 8/062* (2013.01); *A61K 8/375* (2013.01); *A61K 8/463* (2013.01); *A61K 8/922* (2013.01); *A61Q 19/00* (2013.01); *A61K 2800/30* (2013.01); *A61K 2800/34* (2013.01)

(58) Field of Classification Search
CPC ................................ A61Q 19/00; A61Q 19/10
See application file for complete search history.

(56) References Cited

U.S. PATENT DOCUMENTS

| | | |
|---|---|---|
| 2022/0296493 A1 | 9/2022 | Skubsch et al. |
| 2022/0296494 A1 | 9/2022 | Skubsch et al. |

FOREIGN PATENT DOCUMENTS

| | | |
|---|---|---|
| DE | 19938756 A1 | 2/2001 |
| DE | 29924371 U1 | 11/2002 |
| DE | 10148825 A1 | 4/2003 |
| EP | 1935394 A1 | 6/2008 |
| WO | 0200733 A1 | 1/2002 |
| WO | 2007017196 A2 | 2/2007 |
| WO | 2008003685 A1 | 1/2008 |

OTHER PUBLICATIONS

WO2007017196—machine-translation, 2025, machine translation of WO 2007017196.*

* cited by examiner

*Primary Examiner* — Sun Jae Yoo
(74) *Attorney, Agent, or Firm* — Abel Schillinger, LLP

(57) ABSTRACT

The present application relates to a cosmetic emulsion.

20 Claims, No Drawings

ACRYLATE AND SILICONE-FREE COSMETIC O/W EMULSION

BACKGROUND OF THE INVENTION

1. Field of the Invention

The present invention relates to an acrylate and silicone-free cosmetic O/W emulsion

2. Discussion of Background Information

Cosmetic products generally not only serve to appear beautiful and attractive, but their effects make a decisive contribution to increased self-esteem and people's wellbeing. Accordingly, a wide variety of cosmetic products are used for daily cleansing and care of human skin.

Skin care products generally consist of emulsions. Emulsions are generally understood to mean heterogeneous systems composed of two liquids that are immiscible, or of only limited miscibility, with each other, which are typically referred to as phases and in which one of the two liquids is dispersed in the other liquid in the form of very fine droplets. Externally and viewed with the naked eye, emulsions appear homogeneous.

If the two liquids are water and oil and oil droplets are present finely distributed in water, it is an oil-in-water emulsion (O/W emulsion, milk for example). The basic character of an O/W emulsion is influenced by the water. The reverse principle applies to a water-in-oil emulsion (W/O emulsion, butter for example), wherein the basic character in this case is determined by the oil.

To stabilize and thicken O/W emulsions, acrylate-based polymers are usually incorporated into these formulations. Acrylate-based polymers are polymers that are obtained from homo- or copolymerization with acrylic and/or methacrylic acid. Examples include, inter alia, carbomer or acrylate copolymers.

The prior art includes, inter alia, documents DE 10148825 A1, DE 19938756 A1 and DE 29924371 U1, which disclose skincare O/W emulsions with acrylate-based polymers. However, the use of these acrylate-based polymers is increasingly being criticized as their biodegradability has not been fully clarified.

Another frequently used constituent of O/W emulsions for application to skin are silicone oils. When an O/W emulsion is applied, the skin feels supple. In addition, silicone oils have a softening effect and act as an optical wrinkle filler. Silicones are not harmful to the skin per se. As substances foreign to the skin, they do not trigger any allergies or irritation. Once washed off, the skin is as it was before.

However, the fact that the environmental compatibility of silicone oils has not yet been conclusively assessed and that the substances are difficult to degrade in nature is also critical. Consequently, it is important to reduce the use of silicone oils in cosmetic preparations for application to the skin.

However, the problem is that O/W emulsions which do not comprise any acrylate-containing polymers and which do not use silicone oils often tend to leave white residues when they are distributed on the skin.

The object of the present invention, therefore, was to provide an acrylate-free and silicone-free cosmetic O/W emulsion which does not have the disadvantages of the prior art. In particular, it was an object to provide such an O/W emulsion which is rapidly absorbed when applied and has lower amounts of residues.

SUMMARY OF THE INVENTION

Surprisingly, the object(s) is/are achieved by an acrylate-free and silicone-free cosmetic O/W emulsion comprising
  a) at least one substance selected from the group of the alkali metal alkyl sulfates, wherein the alkyl group each comprises 15 to 19 carbon atoms,
  b) hydroxypropyl starch phosphate, and
  c) glyceryl stearate SE.

The invention also relates to the use of a mixture composed of
  a) at least one substance selected from the group of the alkali metal alkyl sulfates, wherein the alkyl group each comprises 15 to 19 carbon atoms,
  b) hydroxypropyl starch phosphate, and
  c) glyceryl stearate SE
in an acrylate- and silicone-free cosmetic O/W emulsion for reducing white residues when the emulsion is applied to the skin.

If percentages by weight (% by weight) are given below without reference to a particular composition or specific mixture, then these figures always refer to the total weight of the cosmetic O/W emulsion. If ratios of components/substances/substance groups are disclosed below, these ratios refer to ratios by weight of the components/substances/substance groups specified.

If ranges of percentages by weight are given below for the constituents of the cosmetic O/W emulsion, the disclosure of the present application also includes all individual values in steps of 0.1% by weight within these weight percentage ranges.

The expressions "according to the invention", "advantageous according to the invention", "advantageous in the context of the present invention" etc. always relate in the context of the present disclosure to both the preparation according to the invention and the use according to the invention.

All experiments were carried out under standard conditions unless stated otherwise. The expression "standard conditions" signifies 20° C., 1013 hPa and a relative humidity of 50%.

If the term skin is used, this preferably refers to human skin.

The O/W emulsion according to the invention is acrylate-free. In the context of the present invention, acrylate-free means that the total proportion of acrylate-based polymers is less than 0.05% by weight and especially preferably 0% by weight, where the figures refer to the total weight of the emulsion. In accordance with the invention, acrylate-based polymers are understood to mean all polymers which are obtained from a homopolymerization or copolymerization with acrylic acid and/or methacrylic acid.

In the context of the present disclosure, silicone-free means that no molecules containing dialkylsiloxane units are present.

According to the invention, the cosmetic O/W emulsion comprises a substance selected from the group of the alkali metal alkyl sulfates, where the alkyl group each comprises 15 to 19 carbon atoms.

Among the alkali metal alkyl sulfates, preference is given to using sodium cetyl sulfate, sodium stearyl sulfate and a mixture thereof known under the name sodium cetearyl sulfate.

A preferred subject matter of the invention is thus an acrylate-free and silicone-free cosmetic O/W emulsion comprising,
- a) at least one substance selected from the group sodium cetyl sulfate, sodium stearyl sulfate and sodium cetearyl sulfate,
- b) hydroxypropyl starch phosphate, and
- c) glyceryl stearate SE.

It is further advantageous according to the invention if the substances mentioned in each case above under a) are present at a total proportion of from 0.05% by weight to 2.0% by weight, more preferably from 0.08% by weight to 1.5% by weight and most preferably from 0.1% by weight to 0.3% by weight, based on the total weight of the emulsion.

It is furthermore advantageous in the context of the present invention if the proportion of hydroxypropyl starch phosphate is from 0.1% by weight to 5% by weight, preferably from 0.15% by weight to 4.0% by weight and particularly preferably from 0.2% to 3% by weight, based on the total weight of the emulsion.

In general, hydroxypropyl starch phosphate is an esterification product based on starch. In accordance with the invention, it is possible to use hydroxypropyl starch phosphate based on different starches. Wheat or potato starch, inter alia, are known to those skilled in the art.

Surprisingly, however, it has been found by those skilled in the art that if the hydroxypropyl starch phosphate used is an esterification product based on corn starch, the O/W emulsion according to the invention is significantly less sticky on the skin than if other starch sources are used. Advantageous embodiments of the present invention are thus characterized in that the hydroxypropyl starch phosphate used is an esterification product based on corn starch. Within these embodiments, it is further preferred when the proportion of hydroxypropyl starch phosphate, which is an esterification product based on corn starch, is from 0.1% by weight to 5% by weight, preferably from 0.15% by weight to 4.0% by weight and particularly preferably from 0.2% by weight to 3% by weight, based on the total weight of the emulsion.

A hydroxypropyl starch phosphate based on corn starch according to the invention is available under the trade name C*HiForm A 12747 from Cargill or Structure® XL from Akzo Nobel Specialty Chemicals.

It is also advantageous according to the invention if the total proportion of glycerin stearate SE is from 0.1% by weight to 6.0% by weight, preferably 0.5% by weight to 5.0% by weight and particularly preferably from 1.0% by weight to 3.0% by weight, wherein the figures refer to the total weight of the emulsion.

Furthermore, it was surprisingly found that emulsions in particular can be stabilized with the combination according to the invention, which are characterized in that the proportion of the oil phase of the emulsion is more than 2% by weight to 30% by weight, preferably more than 3% by weight to 20% by weight and particularly preferably from more than 4% by weight to 15.5% by weight, based on the total weight of the emulsion, where surfactants and emulsifiers are by definition not included in the oil phase, unless they are explicitly assigned to the oil phase in the present disclosure. Therefore, surprisingly, emulsions having a large proportion of oil phases can be stabilized.

In accordance with the invention, emulsifiers and surfactants are not included in the oil phase. This means that glyceryl stearate SE and sodium alkyl sulfates, inter alia, are not included in the oil phase.

Emulsifiers are understood to mean all substances which are listed in the International Cosmetic Ingredient Dictionary and Handbook, Thirteenth Edition 2010, (ISBN 1-882621-47-6) under the designation "emulsifying agent". Surfactants are understood to mean all substances which are listed in the International Cosmetic Ingredient Dictionary and Handbook, Thirteenth Edition 2010, (ISBN 1-882621-47-6) under the designation "surfactant".

In addition, it is advantageous if, in addition to the emulsifier glyceryl stearate SE, the emulsifier glyceryl stearate is also present, where the proportion of glyceryl stearate is preferably from 0.3 to 7% by weight, more preferably from 0.35 to 5% by weight and particularly preferably from 0.5 to 1.5% by weight, based on the total weight of the emulsion.

It has also been shown, surprisingly, that the temperature stability of the O/W emulsion according to the invention could be increased further by adding one or more fatty alcohols having 14 to 22 carbon atoms to the emulsion. The total proportion of these fatty alcohols having 14 to 22 carbon atoms is advantageously from 0.1% by weight to 7.0% by weight, preferably 0.5% by weight to 6.0% by weight and particularly preferably from 1% by weight to 5.0% by weight, based on the total weight of the emulsion. Fatty alcohols having 14 to 22 carbon atoms are included in the oil phase.

Fatty alcohols to be selected with particular preference are cetyl alcohol and/or stearyl alcohol, wherein these are preferably used at proportions from 0.1% by weight to 7.0% by weight, preferably 2% by weight to 6.0% by weight and particularly preferably from 3% by weight to 5.0% by weight, based on the total weight of the emulsion. The mixture of cetyl alcohol and stearyl alcohol is known under the INCI name Cetearyl Alcohol.

Advantageous embodiments of the present invention are further characterized in that the O/W emulsion comprises further polysaccharide-containing polymers.

The O/W emulsion of these embodiments advantageously comprises tapioca starch, wherein the proportion of tapioca starch is preferably in the range from 0.5% by weight to 3.0% by weight, the weight figures referring to the total weight of the O/W emulsion.

In addition, the O/W emulsion of these embodiments advantageously comprises one or more further starch phosphates, wherein the total proportion of these additional starch phosphates is preferably in the range of 0.5% by weight to 3.0% by weight, where the weight figures refer to the total weight of the O/W emulsion. The term "further starch phosphates" is understood to mean starch phosphates which are different from hydroxypropyl starch.

In addition, the O/W emulsion of these embodiments advantageously comprises xanthan and/or modified xanthan, wherein the total proportion of these polymers is in the range from 0.05% by weight to 0.5% by weight, where the weight figures refer to the total weight of the O/W emulsion.

In addition, the O/W emulsion of these embodiments advantageously comprises carrageenan, wherein the total proportion of carrageenan is in the range from 0.05% by weight to 0.5% by weight, where the weight figures refer to the total weight of the O/W emulsion.

Other advantageous embodiments of the present invention are further characterized in that, besides hydroxypropyl starch phosphate, said emulsion comprises no other starches and starch derivatives.

Other advantageous embodiments of the present invention are further characterized in that said emulsion does not comprise any celluloses or cellulose derivatives.

Other advantageous embodiments of the present invention are further characterized in that said emulsion does not comprise any further polysaccharide-containing polymers.

The O/W emulsion according to the invention also advantageously comprises one or more lipid components, such as waxes and oils based on hydrocarbons, saturated, unsaturated or hardened triglycerides, dialkyl ethers having 12 to 24 carbon atoms and/or the esters of monohydric alcohols and monocarboxylic acids having at least 10 carbon atoms.

As already stated, it is advantageous if the O/W emulsion of the present invention does not contain any mineral oil.

It is also advantageous if no branched and/or unbranched hydrocarbons are present. Examples of such hydrocarbons are paraffinum liquidum, isododecane, isohexadecane, isoeicosane, squalane and cera microcristallina.

The O/W emulsion according to the invention advantageously comprises one or more triglycerol esters selected from the group of synthetic, semi-synthetic and natural triglycerol esters.

Natural oils advantageously present are selected from the group *Persea gratissima* oil, *Orbignya oleifera* seed oil, *Argania spinosa* kernel oil, *Prunus armeniaca* kernel oil, *Simmondsia chinensis* seed oil, *Cocos nucifera* oil, *Silybum marianum* seed oil, *Oenothera biennis* oil, *Olea europaea* fruit oil, *Helianthus annuus* seed oil, *Vitis vinifera* seed oil, *Cannabis sativa* seed oil, vegetable oil, *Gossypium herbaceum* seed oil, *Arctium lappa* seed oil, *Macadamia ternifolia* seed oil, *Macadamia integrifolia* seed oil, *Zea mays* germ oil, *Prunus amygdalus dulcis* oil, *Ricinus communis* seed oil, vegetable oil and *Glycine soja* oil.

If the O/W emulsion contains one or more of the natural oils mentioned above, the proportion of these natural oils is preferably from 0.1% by weight to 5.0% by weight, based on the total weight of the O/W emulsion.

It is also advantageous if an oil is present selected from the group coco-caprylate, dicaprylyl ether, coco-glycerides, coco-caprylate/caprate, decyl oleate, caprylic/capric triglycerides, ethylhexyl cocoate, octyldodecanol, squalane, triisostearin, shea butter ethyl esters, ethylhexyl cocoate, decyl cocoate, isoamyl cocoate, caprylyl caprylate/caprate, triheptanoin, hexyldecyl stearate and isoamyl laurate.

Further preferred triglycerol esters include, inter alia, hardened triglyceride fats, such as hydrogenated palm oil, hydrogenated coconut oil or hydrogenated castor oil. Particular preference is given to the use of hydrogenated coconut oil (hydrogenated coco-glycerides), wherein the proportion of hydrogenated coconut oil is preferably from 0.5% by weight to 3% by weight, based on the total weight of the emulsion.

Furthermore, it is particularly advantageous if the emulsion comprises caprylic/capric triglyceride, wherein the proportion of caprylic/capric triglyceride is preferably from 0.5% by weight to 5.0% by weight, based on the total weight of the O/W emulsion.

It is also particularly advantageous if the emulsion comprises coco-glycerides, wherein the proportion of coco-glycerides is preferably from 0.5% to 9% by weight and particularly preferably from 1% to 8% by weight, based on the total weight of the emulsion.

Furthermore, it is advantageous in the context of the present invention if the O/W emulsion of the present invention comprises one or more dialkyl ethers having 12 to 24 carbon atoms, dicaprylyl ether preferably being present. If the O/W emulsion comprises dicaprylyl ether, the proportion of dicaprylyl ether is preferably from 0.5% by weight to 3% by weight, based on the total weight of the O/W emulsion.

Furthermore, it is particularly advantageous in the context of the present invention if the O/W emulsion of the present invention comprises one or more esters of monohydric alcohols and monocarboxylic acids, the esters having at least 10, preferably at least 15 carbon atoms. Esters of monohydric alcohols and monocarboxylic acids to be advantageously selected are 2-ethylhexyl isostearate, isotridecyl isononanoate, 2-ethylhexyl cocoate, $C_{12-15}$-alkyl benzoate, isopropyl myristate and isopropyl palmitate.

It is also advantageous in the context of the present invention if the O/W emulsion comprises octyldodecanol.

It is also particularly advantageous if the emulsion is characterized in that said emulsion comprises coco-caprylate/caprate, wherein the proportion of coco-caprylate/caprate is preferably from 0.5% to 7% by weight and particularly preferably from 2% to 6% by weight, based on the total weight of the emulsion.

Another particularly advantageous constituent of the emulsion is also *Butyrospermum parkii* butter, which is preferably present at a proportion of 0.3% to 2% by weight and particularly preferably 0.5% to 1.5% by weight, based on the total weight of the emulsion.

It is also advantageous according to the invention if the O/W emulsion comprises propylene glycol, butylene glycol, 2-methylpropane-1,3-diol, 1,2-pentanediol, 1,2-hexanediol, 1,2-octanediol glyceryl caprylate and/or 1,2-decanediol.

In addition, it is also advantageous in the context of the present invention if the O/W emulsion comprises phenoxyethanol, dehydroacetic acid, benzyl alcohol and/or ethylhexylglycerin.

If the O/W emulsion comprises benzyl alcohol, it is preferred if the proportion of benzyl alcohol is from 0.1% by weight to 0.5% by weight, based on the total weight of the O/W emulsion.

If the O/W emulsion comprises phenoxyethanol, it is preferred if the total proportion of phenoxyethanol is from 0.1% by weight to 1.2% by weight, based on the total weight of the O/W emulsion.

If the O/W emulsion comprises ethylhexylglycerin, it is preferred if the proportion of ethylhexylglycerin is from 0.1% by weight to 1.0% by weight, based on the total weight of the O/W emulsion.

It is also advantageous if embodiments of the invention are characterized in that these comprise ethanol. If ethanol is present in the O/W emulsion, the proportion of ethanol is preferably from 0.5% by weight to 10% by weight, based on the total weight of the O/W emulsion.

Furthermore, the O/W emulsion according to the invention is preferably characterized in that said emulsion comprises glycerol at a proportion of 0.5% by weight to 15% by weight, based on the total weight of the O/W emulsion.

Furthermore, it is preferred if the O/W emulsion only comprises further surfactants and/or emulsifiers at a maximum proportion of 2% by weight, preferably at a maximum proportion of 1.5% by weight, where the figures refer to the total weight of the emulsion.

Last but not least, embodiments advantageous according to the invention are characterized in that the O/W emulsion comprises one or more active ingredients selected from the group of the compounds comprising glycyrrhetic acid, urea, arctiin, folic acid, coenzyme Q10 (ubiquinone), alpha-glucosylrutin, carnitine, carnosine, caffeine, natural and/or synthetic isoflavonoids, glycerylglucose, creatine, creatinine, taurine, tocopherol, tocopherol acetate, vitamin C, vitamin C phosphate, vitamin C palmitate, niacinamide, vitamin A palmitate, panthenol, licochalcone A, rucinol, N-[(2,4-dihydroxyphenyl)thiazol-2-yl]isobutyramide, honokiol and magnolol (also as constituent of magnolia extracts), hyaluronic acid and/or silymarin (milk thistle extract).

Furthermore, O/W emulsions advantageous according to the invention are characterized in that said emulsions comprise water at a proportion of 60% by weight to 95% by weight and preferably from 70% by weight to 90% by weight, based on the total weight of the emulsion.

Furthermore, O/W emulsions advantageous according to the invention have a viscosity of 3000 mPa·s to 6000 mPa·s 24 hours after preparation. If viscosity is referred to in this disclosure, all values relate to measurement at 25° C. in a 150 ml snap-lid bottle using a Rheomat R 123 from proRheo. The Rheomat R 123 from proRheo GmbH is a rotational viscometer, i.e. a measurement bob rotates in the substance to be measured. The force is measured that is required to rotate the measurement bob in the sample at a predefined speed. From this torque, the speed of the measurement bob and the geometric dimensions of the measuring system used, the viscosity is calculated. The measurement bob used is measurement bob No. 1 (article no. 200 0191), speed range 62.5 min$^{-1}$. All viscosity measurements are carried out 24 hours after preparation of the O/W emulsion.

DETAILED DESCRIPTION OF EXEMPLARY EMBODIMENTS OF THE INVENTION

Comparative Experiments and Examples

The examples below are intended to illustrate the present invention without limiting it. Unless otherwise stated, all quantitative data, fractions, and percentages are based on the weight and the total amount or on the total weight of the preparations.

The following table shows with Comp. 1 and Comp. 2 two emulsions not according to the invention, while Ex. 1 represents an emulsion according to the invention. The properties of Comp. 1 and Comp. 2 were compared to Ex. 1. When applying the emulsions to the skin, a panel of experts found that Comp. 1 and Comp. 2 leave significant amounts of white residue when applied to the forearm. In contrast, Ex. 1 shows almost no white residues.

| Ingredient | Comp. 1 | Comp. 2 | Ex. 1 |
|---|---|---|---|
| Sodium cetearyl sulfate | 0.15 | 0.15 | 0.15 |
| Glyceryl stearate SE | 1.5 | 1.5 | 1.5 |
| Glyceryl stearate | 1 | 1 | 1 |
| Cetearyl alcohol | 4 | 4 | 4 |
| *Butyrospermum parkii* butter | 1 | 1 | 1 |
| Coco glycerides | 6 | 6 | 6 |
| Coco caprylate | 4 | 4 | 4 |
| Carbomer | 0.1 | | |
| Hydroxypropyl starch phosphate | | | 1 |
| Xanthan gum | | 0.5 | |
| Glycerol | 7 | 7 | 7 |
| Phenoxyethanol | 0.9 | 0.9 | 0.9 |
| Ethylhexylglycerin | 0.2 | 0.2 | 0.2 |
| 45% sodium hydroxide solution | 0.06 | | |
| Aqua | to 100 | to 100 | to 100 |
| White residue after application to the forearm | Significant | Very significant | Sparse |
| Viscosity 24 hours after preparation, 25° C. | 4650 mPas | 3250 mPas | 4550 mPas |
| Stability, storage at 40° C. for 1 month | OK | OK | OK |
| Stability, storage at 50° C. for 1 month | OK | Sharp water separation | OK |

The abbreviation OK above signifies in order; no phase separation was found.

The further examples are intended to illustrate the invention further without limiting it.

| Ingredients | Ex. 2 | Ex. 3 | Ex. 4 | Ex. 5 | Ex. 6 | Ex. 7 |
|---|---|---|---|---|---|---|
| Sodium cetearyl sulfate | 0.15 | 0.25 | 0.15 | 0.15 | 0.2 | 0.05 |
| Glyceryl stearate SE | 1.5 | 3 | 3 | 1.5 | 1.5 | 2.5 |
| Glyceryl stearate | 1 | 1 | | 1 | 1 | 1 |
| Cetearyl alcohol | 4 | 3 | 3.5 | | 4 | 4 |
| Stearyl alcohol | | | | 3 | | |
| *Butyrospermum parkii* butter | 1 | 1 | | 1 | | 1 |
| Coco caprylate/caprate | | 3 | 2 | | | |
| Coco glycerides | 3 | | 6 | 1 | | 6 |
| Coco caprylate | | 4 | | 4 | 4 | 4 |
| *Helianthus annuus* seed oil | 2 | | | | | |
| Dicaprylyl ether | 3 | 2 | 2 | | | |
| Ethylhexyl cocoate | | | | 3 | 2 | |
| Hydroxypropyl starch phosphate | 1 | 0.5 | 1 | 0.7 | 1.5 | 2 |
| Glycerol | 7 | 8 | 5 | 6 | 5 | 7 |
| Phenoxyethanol | 0.9 | 0.9 | | 0.9 | | 0.5 |
| Ethylhexylglycerin | 0.2 | 0.2 | | | 0.2 | |
| Glyceryl caprylate | | | 0.3 | | | 0.3 |
| Glyceryl caprate | | | 0.5 | | | |
| Alcohol | | | 3.0 | | | |
| Perfume | 0.2 | | | 0.4 | | 0.3 |
| Aqua | to 100 | to 100 | to 100 | to 100 | to 100 | to 100 |

| Ingredients | Ex. 8 | Ex. 9 | Ex. 10 | Ex. 11 | Ex. 12 | Ex. 13 |
|---|---|---|---|---|---|---|
| Sodium cetearyl sulfate | 0.15 | 0.1 | 0.15 | 0.2 | 0.1 | 0.15 |
| Glyceryl stearate SE | 2 | 2.5 | 3.0 | 1.5 | 2.5 | 2.5 |
| Glyceryl stearate | | | | 1 | | |
| Cetearyl alcohol | 4 | 4 | 3.5 | 2.5 | 5 | 3 |
| Cetyl palmitate | | | 1.0 | | | |
| Dicaprylyl ether | | 3 | | | | |
| Caprylic/capric triglycerides | | | | 4 | 3 | |
| Coco caprylate/caprate | 4 | | 3 | | 2 | |
| Vegetable oil | | | 4 | | | 3 |
| *Theobroma cacao* seed butter | | | 1 | | | |
| Octyldodecanol | 3 | 3.0 | | | | |
| Undecane/tridecane | | | | | | 3 |
| Hydroxypropyl starch phosphate | 0.4 | 0.5 | 0.5 | 0.8 | 1 | 0.7 |
| Glycerol | 5 | 6 | 7 | 7 | 5 | 8 |
| Phenoxyethanol | 0.5 | | 1 | | 0.8 | |
| Alcohol Denat. | | 2 | 2 | 2 | | 1 |
| Citric acid | 0.2 | | | 0.3 | | |
| Caprylyl glycol | | 1.0 | | | | |
| Ethylhexylglycerin | | | 0.5 | | | |
| Benzyl alcohol | | | | | 0.3 | |
| Sodium phytate | | | 0.2 | | | |
| Perfume | | | 0.4 | | | |
| Aqua | to 100 | to 100 | to 100 | to 100 | to 100 | to 100 |

| Ingredients | Ex. 14 | Ex. 15 | Ex. 16 |
|---|---|---|---|
| Sodium cetearyl sulfate | 0.2 | 0.15 | 0.15 |
| Glyceryl stearate SE | 1.5 | 1.5 | 1 |
| Glyceryl stearate | | 3 | 5 |
| Cetearyl alcohol | | 4.5 | |
| Cetyl alcohol | 2 | | |
| Stearyl alcohol | 2 | | 4 |
| Caprylic/capric triglycerides | | | 2 |
| Octyldodecanol | 3 | | |
| Triisostearin | | 1 | |
| *Prunus amygdalus dulcis* oil | | 2 | |
| Vegetable oil | 0.9 | 0.4 | 3 |
| Hydrogenated coco glycerides | 1 | 0.5 | 1 |
| *Butyrospermum parkii* butter | 0.5 | | 1 |
| Hxdroxypropyl starch phosphate | 0.75 | 1 | 2 |
| Tapioca starch | | | 2 |
| Xanthan gum | | | 0.1 |
| Ethylhexylglycerin | 0.5 | 0.3 | 0.1 |
| Glycerol | 8 | 5 | 15 |
| Alcohol | 3 | 4 | 5 |
| Perfume | 0.2 | 0.3 | 0.4 |
| Aqua | to 100 | to 100 | to 100 |

What is claimed is:

1. A cosmetic oil-in-water (O/W) emulsion, wherein the emulsion is acrylate- and silicone-free and comprises
    (a) at least one substance selected from alkali metal alkyl sulfates, wherein the alkyl group comprises 15 to 19 carbon atoms,
    (b) hydroxypropyl starch phosphate, and
    (c) glyceryl stearate SE.

2. The emulsion of claim 1, wherein (a) comprises one or more of sodium cetyl sulfate, sodium stearyl sulfate, and sodium cetearyl sulfate.

3. The emulsion of claim 1, wherein the emulsion comprises from 0.05% by weight to 2.0% by weight of (a), based on a total weight of the emulsion.

4. The emulsion of claim 3, wherein the emulsion comprises from 0.08% by weight to 1.5% by weight of (a).

5. The emulsion of claim 1, wherein the emulsion comprises from 0.1% by weight to 5% by weight of (b), based on a total weight of the emulsion.

6. The emulsion of claim 5, wherein the emulsion comprises from 0.15% by weight to 4% by weight of (b).

7. The emulsion of claim 1, wherein the emulsion comprises from 0.1% by weight to 6.0% by weight of (c), based on a total weight of the emulsion.

8. The emulsion of claim 7, wherein the emulsion comprises from 0.5% by weight to 5.0% by weight of (c).

9. The emulsion of claim 1, wherein an oil phase concentration is from more than 2% by weight to 30% by weight, based on a total weight of the emulsion.

10. The emulsion of claim 9, wherein an oil phase concentration is from more than 3% by weight to 20% by weight.

11. The emulsion of claim 1, wherein the emulsion further comprises glyceryl stearate.

12. The emulsion of claim 11, wherein the emulsion comprises from 0.3% by weight to 7% by weight of glyceryl stearate, based on a total weight of the emulsion.

13. The emulsion of claim 1, wherein the emulsion further comprises one or more fatty alcohols having from 14 to 22 carbon atoms.

14. The emulsion of claim 1, wherein the emulsion does not contain mineral oil.

15. The emulsion of claim 1, wherein the emulsion further comprises coco glycerides.

16. The emulsion of claim 1, wherein the emulsion further comprises coco caprylate/caprate.

17. The emulsion of claim 1, wherein the emulsion further comprises *Butyrospermum parkii* butter.

18. The emulsion of claim 1, wherein the emulsion comprises not more than 2% by weight of further surfactants and/or emulsifiers, based on a total weight of the emulsion.

19. The emulsion of claim 1, wherein the emulsion has a viscosity of 3,000 mPa·s to 6,000 mPa·s 24 hours after preparation at 25° C., as determined with a Rheomat R 123 from ProRheo using measuring bob 1 at a speed of 62.5 $min^{-1}$.

20. A method of reducing white residues caused by applying an acrylate- and silicone-free O/W emulsion onto skin, wherein the method comprises including in the emulsion a mixture of (a) at least one substance selected from alkali metal alkyl sulfates, wherein the alkyl group comprises 15 to 19 carbon atoms,
(b) hydroxypropyl starch phosphate, and
(c) glyceryl stearate SE.

* * * * *